United States Patent
Tai et al.

(10) Patent No.: US 10,371,640 B2
(45) Date of Patent: Aug. 6, 2019

(54) COMPOSITIONS AND METHODS FOR LEUKOCYTE DIFFERENTIAL COUNTING

(71) Applicant: CALIFORNIA INSTITUTE OF TECHNOLOGY, Pasadena, CA (US)

(72) Inventors: Yu-Chong Tai, Pasadena, CA (US); Wendian Shi, Sierra Madre, CA (US); Harvey Kasdan, Jerusalem (IL)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/647,039

(22) Filed: Jul. 11, 2017

(65) Prior Publication Data
US 2017/0315060 A1 Nov. 2, 2017

Related U.S. Application Data

(62) Division of application No. 13/686,866, filed on Nov. 27, 2012, now abandoned.

(60) Provisional application No. 61/580,761, filed on Dec. 28, 2011, provisional application No. 61/564,120, filed on Nov. 28, 2011.

(51) Int. Cl.
*G01N 21/64* (2006.01)
*G01N 21/05* (2006.01)
*G01N 21/03* (2006.01)

(52) U.S. Cl.
CPC ..... *G01N 21/6486* (2013.01); *G01N 21/6428* (2013.01); *G01N 21/05* (2013.01); *G01N 2021/0346* (2013.01); *G01N 2021/6441* (2013.01); *G01N 2021/6482* (2013.01)

(58) Field of Classification Search
CPC ............ G01N 33/582; G01N 33/5005; G01N 33/5094; G01N 15/14; G01N 2021/6439; G01N 21/6428; G01N 21/6486; G01N 2500/10; G01N 33/533
See application file for complete search history.

(56) References Cited

U.S. PATENT DOCUMENTS

| | | |
|---|---|---|
| 3,916,205 A | 10/1975 | Kleinerman |
| 4,400,370 A | 8/1983 | Kass |
| 5,296,378 A | 3/1994 | Sakata et al. |
| 5,434,081 A | 7/1995 | Maekawa |
| 6,004,816 A | 12/1999 | Mizukami et al. |
| 6,197,593 B1 | 3/2001 | Deka et al. |
| 2004/0185447 A1 | 9/2004 | Maples et al. |
| 2009/0042241 A1 | 2/2009 | Yu-Chong et al. |

OTHER PUBLICATIONS

Crissman, H. et al., "Simplified method for DNA and protein staining of human hematopoietic cell samples," Cytometry, 1981, 2(2):59-62.
O'Connor, A. et al., "Fluorescence filter combinations," Nikon Microscopy U, 2004, 1-5.
PCT Application No. PCT/US2012/066655, International Search Report, dated Mar. 13, 2013, 3 pages.
Shi, W. et al., "Four-part differential leukocyte count using microflow cytometer," MEMS 2010: 23rd IEEE International Conference on Micro Electro Mechanical Systems, Hong Kong, Jan. 25-28, 2010, pp. 1019-1022.
Shi, W. et al., "Leukocyte 5-part differential count using a microfluidic cytometer," Solid-State Sensors, Actuators and Microsystems Conference (TRANDUCERS), 2011 16th International, Beijing, China, Jun. 5-9, 2011, pp. 2956-2959.
Zheng, S. et al., "Fluorescent labeling, sensing, and differentiation of leukocytes from undiluted whole blood samples," Sensors and Actuators B, Jun. 16, 2008, vol. 132, No. 2, pp. 558-567.

*Primary Examiner* — Lynn Y Fan
(74) *Attorney, Agent, or Firm* — Kilpatrick Townsend & Stockton LLP

(57) ABSTRACT

The present invention provide compositions and methods for classifying leukocytes in a leukocyte population using fluorescence detection. The methods include contacting a leukocyte population in a sample having one or more leukocyte types with a diagnostic composition, exciting the leukocyte population with a light source; and measuring emitted light from each of the one or more leukocyte types to classify the leukocyte population.

15 Claims, 6 Drawing Sheets

US 10,371,640 B2

COMPOSITIONS AND METHODS FOR LEUKOCYTE DIFFERENTIAL COUNTING

CROSS-REFERENCE TO RELATED APPLICATIONS

This application is a divisional of U.S. application Ser. No. 13/686,866, filed Nov. 27, 2012, pending, which application claims priority to U.S. Provisional Patent Application Nos. 61/580,761, filed Dec. 28, 2011 and 61/564,120, filed Nov. 28, 2011, the teachings all of which are hereby incorporated by reference in their entireties for all purposes.

STATEMENT REGARDING FEDERALLY SPONSORED RESEARCH OR DEVELOPMENT

This invention was made with government support under NCC 9-58 NSBRI(TD01301) MSC-25107 awarded by NASA Johnson Space Center. The government has certain rights in the invention.

BACKGROUND OF THE INVENTION

White blood cell (WBC) differential count is a clinical analysis that enumerates the total number of leukocytes in a per volume blood sample, and classifies the leukocyte population into different types or subpopulations, such as lymphocytes, monocytes, neutrophils, eosinophils and basophils. The analysis is useful for diagnoses of diseases such as leukemia, infections and allergies.

Presently, automated leukocyte differential counting is conducted in a hematology analyzer or in flow cytometer by utilizing differences in cell morphologies or cellular contents. The analysis of cell morphologies use detection methods such as light scattering and electrical impedance of individual cells. Alternatively, leukocytes can be analyzed based on their cellular contents, which can be selectively stained by fluorescent dyes and detected by corresponding fluoresence emissions, such as by the described reagents and methods in the disclosures of U.S. Pat. Nos. 6,197,593, 6,004,816, 5,296,378, and 5,434,081, 3,916,205.

In recent years, there is increasing interests of miniaturizing the leukocyte differential counting for newly emerging applications such as for NASA spaceflights and bedside healthcare. The previous mentioned reagents and methods for leukocyte analysis are all developed for macro-sized hematology analyzers and flow cytometers, but not optimized for miniaturization applications. For example, the previously mentioned reagents and methods for leukocyte classification either requires a combination of the light scattering detection and the fluorescence detection, or uses multiple steps of exposure and fluorescence detection, which increases system complexity and are difficult to be used in miniaturized instruments. Therefore, there still exists a need in the art for compositions and methods for leukocyte differential counting especially for miniaturization purposes.

BRIEF SUMMARY OF THE INVENTION

The present invention meets the need in the art of new methods for leukocyte differential counting by providing a diagnostic composition, which is a fluorescent dye mixture. The present disclosure relates to a white blood cell (WBC) differentiation composition and method of use thereof, and more particularly to a reagent and method for automatic differentiation of various subgroups of white blood cells in a sample (e.g., blood) using a suitable apparatus such as a flow cytometry system with optics and electronics, or a fully automated hematology analyzer or a microfluidic device. Advantageously, the diagnostic composition is useful to classify at least five different leukocyte types or subpopulations (e.g., lymphocytes, monocytes, neutrophils, eosinophils and basophils) with fluorescence detection as the means of detection. The present invention also provides methods of utilizing the diagnostic compositions with fluorescence detection for leukocyte analysis particularly on a microfluidic cytometer for point-of-care diagnostics.

As such, in one embodiment, the present invention provides a diagnostic composition, comprising, consisting essentially of, or consisting of:
a first dye having a cationic charge;
a second dye having less of a cationic charge compared to the first dye; and
a third dye being reactive to a protein, having an affinity to a protein or having an anionic charge.

In certain aspects, the first dye has at least two cationic charges, whereas the second dye has one cationic charge.

In another embodiment, the present invention provides a method for classifying leukocytes in a leukocyte population with fluorescence detection, comprising:
contacting a leukocyte population in a sample having one or more leukocyte types with a diagnostic composition to form a stained leukocyte population;
exciting the stained leukocyte population with a light source; and
measuring emitted light from each of the one or more leukocyte types in the population to classify the leukocyte population.

These and other objects, features and embodiments will become more apparent when read with the detailed description and figures that follow.

DETAILED DESCRIPTION OF THE INVENTION

I. Embodiments

The present invention provides a diagnostic composition useful in methods for leukocyte differential counting on a microfluidic cytometer using fluorescence detection as a means for detection. By staining the sample with the present dye composition and flowing the stained sample through a microfluidic cytometer, the fluorescent emission of each leukocyte cell type in the population can be individually measured. In this way, the total number of leukocyte cells can be enumerated and different types of leukocytes or subpopulations can be classified to achieve a leukocyte differential count.

Figure 1:
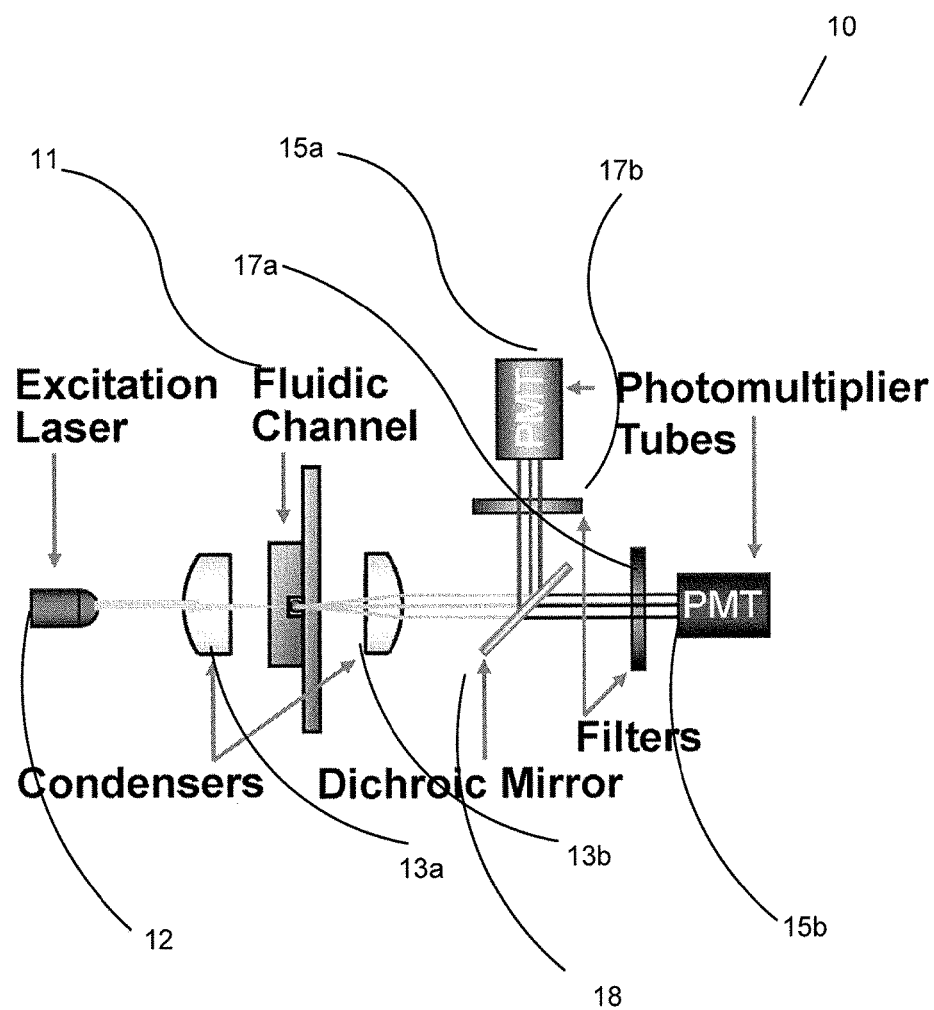
FIG. 1 illustrates an embodiment of an optical configuration of the present invention.

FIG. 1 shows an example of an optical configuration for a microfluidic cytometer 10 of the present invention. As shown therein, a microfluidic cytometer has an excitation laser 12 and a microfluidic chip 11 downstream of the excitation laser. The chip has a fluidic channel for flowing a sample having leukocytes (e.g., a leukocyte population) to be classified and counted into subpopulations or types. During operation, the sample is excited by the excitation laser. At least two photomultiplier tubes 15a, 15b measure emitted fluorescence. The microfluidic cytometer 10 further comprises a first condenser 13a upstream of the microfluidic chip to focus the laser. In addition, the microfluidic cytometer 10 further comprises a second condenser 13b downstream of the microfluidic chip to expand the light and focus the light on a dichroic mirror 18. The microfluidic cytometer 10 preferably has light filters 17a, 17b upstream of each of the two photomultiplier tubes.

Figure 2:
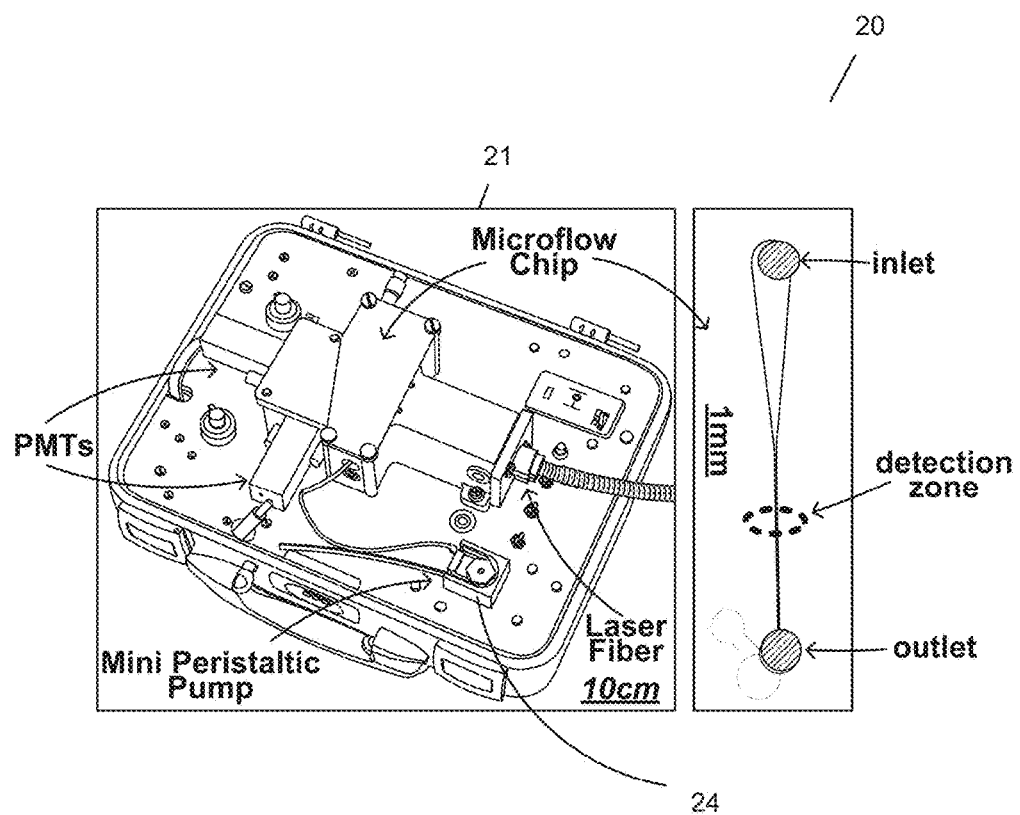
FIG. 2 shows one embodiment of a microfluidic cytometer of the present invention.

FIG. 2 illustrates one example of a microfluidic cytometer 20 using an optical configuration of the present invention. In certain aspects, the microfluidic cytometer has a replaceable microfluidic chip 21, wherein the sample is driven by a peristaltic pump 24. In certain aspects, the microfluidic cytometer 20 can have the fluorescence detection being performed with the same or a similar optical configuration as shown in FIG. 1. The detection fluidic channel (e.g., 28 µm high, 32 µm wide and 40 µm long) is microflow chip, which is optionally replaceable.

In one aspect, a 488 nm 20 mW laser is used as the excitation light source. However, the light source is not limiting. Green fluorescence (e.g., wavelength 510 nm-560 nm) and red fluorescence (wavelength>590 nm) are measured simultaneously by two photomultiplier tubes with optical filters to choose the right wavelength range. The sample (e.g., whole blood) is stained by a diagnostic composition and is flowed through a flow cytometer, wherein stained cells are exposed to an excitation light source, and the intensities of the two color fluorescence from leukocyte cells are recorded.

In one embodiment, the present invention provides a diagnostic composition, comprising, consisting essentially of, or consisting of:
 a first dye having a cationic charge(s);
 a second dye having less of a cationic charge compared to the first dye; and,
 a third dye being reactive to a protein, having an affinity to a protein or having an anionic charge.

In certain aspects, the first dye has at least two cationic charges, whereas the second dye has one cationic charge. For example, the first dye can be propidium iodide and the second dye may be Basic Orange 21. In certain aspects, the third dye is fluorescein isothiocyanate.

For example, the chemical structure for propidium iodide is as follows:

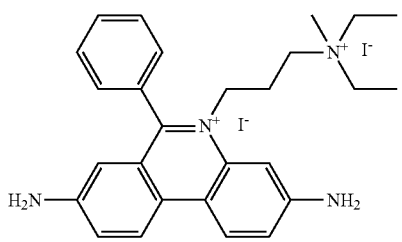 [SMILES: CC[N+](C)(CC)CCC[n+]1c(-c2ccccc2)c2cc(N)ccc2c2ccc(N)cc21 ; [I-] ; [I-]]

The compound has two quaternary nitrogen atoms and at a pH of about 6-8, such as 7.0, the molecule has two cationic charges. Propidium iodide is an intercalating agent and a fluorescent molecule and when bound to a nucleic acid, the fluorescence excitation maximum is 535 nm and the emission maximum is 617 nm.

The second dye has less cationic character than the first dye. For example, the second dye can be Basic Orange 21, which has the following structure:

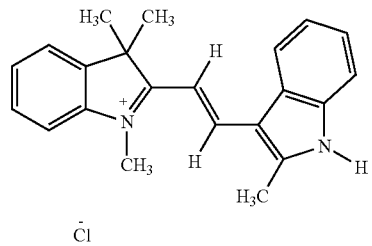

Basic Orange 21 has one quaternary nitrogen and thus in certain aspects, only one charge compared to the first dye.

In certain aspects, the third dye is an anionic dye, such as fluorescein isothiocyanate, which at physiological pH is anionic and is reactive with amine groups of proteins (e.g., an N-terminus, an arginine, a histadine or a lysine). Fluorescein isothiocyanate has the following structure:

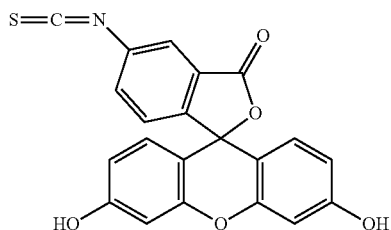 [SMILES: O=C1OC2(c3ccc(O)cc3Oc3cc(O)ccc32)c2ccc(N=C=S)cc21]

Fluorescein isothiocyanate (FITC) is a derivative of fluorescein. FITC has excitation and emission spectrum peak wavelengths of approximately 495 nm/521 nm.

In certain aspects, the present invention provides a mixture of three fluorescent dyes, a first cationic dye carries two or more positive charges such as propidium iodide, a second cationic dye carries less positive charge (e.g., 1 positive charge) than the first dye such as Basic Orange 21, and either an anionic dye or a derivative of an anionic dye or a dye reactive toward proteins such as fluorescein isothiocyanate, which is anionic. This diagnostic composition can be used to selectively stain the nucleus such as nucleic acid, the acidic cytoplasm and protein contents of leukocytes, respectively for Dye 1, Dye 2 and Dye 3, and classify different types of leukocytes. It is believed that the dyes in the composition combine with the cellular constituents (nucleic acid, cytoplasm and proteins) in the leukocytes by ionic adsorption. The fluorescent dye compound that binds to intracellular nucleic acids such as DNA and RNA emits fluorescence. The fluorescence property is a parameter that reflects the amount of fluorescent dye inside the cells in the blood sample. Because differences in the metabolic activities of various subgroups of cells lead to differences in the nucleic acid content or other cellular components, the fluorescence properties of the various subgroups of white blood cells differ in some aspects.

In certain aspects, the charge of the dyes is assessed using techniques known in the art. For example, by using electrophoresis techniques at a standard pH (such as pH 5.0 to 8.0, i.e., pH=5, 6, 7 or 8) it is possible to assess the charge of the dyes. In one aspect, the first dyes has the greatest cationic character and the third dye has the least cationic character. The second dye is in between. In other aspects, the third dye has the greatest anionic character and the first dye has the least anionic character. The second dye is in between.

Other red fluorescent dyes useful for the first cationic dye include for example, the SYTO® dyes from Molecular Probes. These dyes include, for example, red fluorescent SYTO® dyes (SYTO® 17 and SYTO® 59, 60, 61, 62, 63 and 64), each supplied as solutions in dimethylsulfoxide (DMSO). In another aspect, the first dye isdiamidinophenylindole (DAPI). In certain other aspects, the second cationic dye can be, for example, ethidium bromide or the SYTO® Orange Fluorescent Nucleic Acid Stains such as SYTO® 80, 81, 82, 83, 84 or 85 dyes. Green cationic dyes include, for example, SYTO® 9, 11, 12, 13, 14, 16, 18, 21, 24, or SYTO® 25. The present invention provides other anionic protein stains suitable for the present invention such as isomers of fluorescein isothiocyanate (FITC). For example, the thiocyanate group can be on the 4-carbon of the phenyl portion of FITC or the 5-carbon of the phenyl portion of FITC. Those of skill in the art will know of other isomers of FITC.

In certain other aspects, a dye similar to FITC, which has affinity or is reactive towards a protein includes, but is not limited to, [i] fluorescein derivatives, e.g. fluorescamine (FC), [ii] rhodamine and its derivatives, e.g. tetramethylrhodamin isothiocyanate (TRITC), tetramethylrhodamin succinimidyl ester (RHS), and rhodamine isothiocyanate (XRITC), as well as [iii] eosin and its derivatives (e.g. isothiocyanate (EITC)). In certain other aspects, the third dye includes dyes which ionically bind to proteins such as sulforhodamine 101.

In another aspect, the present invention provides a method for classifying leukocytes with fluorescence detection. When leukocytes are stained by the present composition, the intensities of the leukocytes' fluorescence are measured. Typically, the first dye stains the nucleus such as the nucleic acid therein. The second dye having less cationic character than the first dye stains the cytoplasm. The protein contents are stained by the third dye such as an anionic dye or a derivative of an anionic dye such as fluorescein isothiocyanate. The fluorescence is measured to classify different types of leukocytes including lymphocytes, monocytes, neutrophils, eosinophils and basophils. In other aspects, the subpopulations or types of WBC include, for example, lymphocytes, neutrophils, eosinophils, basophils, monocytes, immature granulocytes, abnormal lymphocytes, blast cells, band cells, myelocytes, promyelocytes and metamyelocytes.

In another aspect, the first dye is preferably a red fluorescent dye and the second dye is preferably a green or an orange fluorescent dye. It is important that the first cationic dye carries more positive charges than the second cationic dye. In this way, the primary cationic dye stains the nucleus such as DNA and RNA and the second cationic dye stains the acidic cytoplasm contents. The anionic dye or the derivative of an anionic dye is preferably a green fluorescent dye. The third dye stains the protein contents of leukocyte, as well as the eosinophil granules with a high affinity. In one particular embodiment, the second cationic dye is preferably Basic Orange 21, which has high affinity binding to the heparin contents in the basophils granules. This selective staining of the basophils granules can be used to improve the basophil classification. Thus, in one aspect, the present invention provides an improved method for differentiating between leukocyte populations by fluorescence cytometry. More specifically, in one embodiment, the method permits enumerating and distinguishing between different white blood cell (WBC) subpopulations or types in a biological sample based on nucleic acid, cytoplasmic and protein staining along with fluorescence measurement at two or more wavelengths.

In the present methods, the leukocytes are stained with a dye reagent and exposed to a light excitation source such as a blue or a green-blue light excitation source for fluorescence detection. Two color fluorescence including green fluorescence and red fluorescence are measured for leukocyte analysis. Among different types of leukocytes, eosinophils have the highest green fluorescence, neutrophils have medium green fluorescence, lymphocytes, monocytes and basophils have relatively low green fluorescence, which is due to the differences of the amount of acidic cytoplasm and protein contents. Among lymphocytes, monocytes and basophils, basophils have relatively low red fluorescence, lymphocytes have medium red fluorescence and monocytes have the highest red fluorescence, which is due to the difference of the amount of nucleic acid in the nucleus. In this way, at least five different types of leukocytes, including lymphocytes, monocyte, neutrophils, eosinophil and basophil, can be classified from each other. In one particular embodiment, a third color of fluorescence such as orange-red fluorescence can be used to measure and improve basophil classification, as basophils contain a certain amount of heparin, which is selectively stained and emits the orange-red fluorescence under a green-blue excitation.

In another embodiment, two-color fluorescence of individual leukocyte cells is measured in a microfluidic channel, the size of which is "compatible" to the size of the blood cells. In this way, the leukocyte cells in the blood sample are measured one by one, the total number of the leukocyte cells is enumerated and different types of leukocytes are classified according to their fluorescence intensities. The term "compatible" means the cross-section area of the microfluidic channel is large enough that blood cells can flow through without jamming the channel, and small enough to minimize the coincidence error of the leukocyte count.

The present invention provides a method for classifying leukocytes with fluorescence detection. Advantageously, using the methods of the present invention each of the one or more leukocyte types is distinguishable from each of the other types in the population. In certain instances, the leukocyte types include a lymphocyte, a monocyte, a neutrophil, an eosinophil and a basophil. In certain other aspects, the number of leukocyte types or subpopulations in the leukocyte population is 1, 2, 3, 4, 5, 6, 7, 8, 9, 10 or more leukocyte types or subpopulations. In certain aspects, the number of types of leukocytes is 5 or more, or at least 5, or only 5 types. The fluorescence emitted from each of the leukocyte types is distinguishable from each of the other types in the population. In certain aspects, the leukocytes in the population comprise a lymphocyte, a monocyte, a neutrophil, an eosinophil and a basophil.

In other aspects, the excitation light is emitted from a source selected from the group of a diode laser, a light emitting diode (LED), an ion laser, a dye laser, or a lamp.

In a preferred aspect, the emitted light is measured at two or more wavelengths such as at a first wavelength and at a second wavelength to achieve two color fluorescence measurement. The first wavelength is at about 480 to about 580 nm such as about 480, 490, 500, 510, 520, 530, 540, 550, 560, 570, or 580 nm. In another aspect, the first wavelength is measured at about 500 nm to about 570 nm, or about 510 nm to about 560 nm.

In certain aspects, the second excitation light is emitted and measured at about 590 nm to about 650 nm, such as 590, 600, 610, 620, 630, 640, or 650 nm. In another aspect, the second wavelength is about 590 nm to about 640 nm. The emitted light is measured at the first and the second wavelength. In one aspect, the emitted light is measured simultaneously by two photomultiplier tubes. The sample can be whole blood, plasma, or serum. Preferably, the sample is a whole blood sample.

In certain aspects, the sample is stained by the diagnostic composition and is flowed through a flow cytometer, wherein the one or more leukocyte types is exposed to the light source and the intensities of the fluorescence is recorded. Alternatively, the sample is stained by the diagnostic composition and is flowed through a microfluidic cytometer. In certain aspects, the sample is flowed through the detection channel. In one aspect, the one or more leukocyte types is exposed to the light source one by one, and two color fluorescence emission from each individual leukocyte type is recorded.

In certain aspects, the population of leukocytes is enumerated and the one or more leukocyte types are classified to achieve a leukocyte differential count.

In certain embodiments, the present invention provides a composition and methods for leukocyte analysis, wherein the sample can be a whole blood sample, or another fluid comprising leukocytes. The other fluids can be a blood component such as plasma or serum, bone marrow, or other body fluids such as urine or saliva. The types of leukocytes include, for example, lymphocyte, monocyte, neutrophil, eosinophil, basophil, immature granulocytes, abnormal lymphocytes, blast cells, band cells, myelocytes, promyelocytes and metamyelocytes. Other cells may be present in the sample, such as red blood cells and platelets in a whole blood sample.

In certain embodiments, when employing the compositions and methods to enumerate leukocytes and classify leukocyte types, the dye concentrations of the mixture is about between 0.1 µM to 500 µM, such as 1.0 µM to 100 µM, or 10 µM to 100 µM or 100 µM to 500 µM, for the first dye (primary cationic dye such as propidium iodide); between 1 µM to 2 mM such as 1 µM to 1 mM, or 10 µM to 500 µM for the second dye (secondary cationic dye) such as Basic Orange 21; and between 0.5 µM to 1 mM such as 1 µM to 900 µM or 10 µM to 500 µM for the third dye (the anionic dye or the derivative of an anionic dye) such as fluorescein isothiocyanate.

For example, the first dye can be between 0.1 µM to 500 µM. This includes 1, 10, 20, 30, 40, 50, 60, 70, 80, 90 100, 150, 175, 200, 250, 275, 300, 350, 375, 400, 450, 475 or 500 µM and all the numbers in between. The second dye can be between 1 µM to 2 mM, which includes 1, 2, 3, 4, 5, 6, 7, 8, 9 10, 100, 200, 300, 400, 500, 600, 700, 800, 900 µM, 1 mM, 1.1, 1.2, 1.3, 1.4, 1.5, 1.6, 1.7, 1.8, 1.9 or 2 mM and all the numbers in between. The third dye can be between 0.5 µM to 1 mM such as 1, 2, 3, 4, 5, 6, 7, 8, 9 10, 100, 200, 300, 400, 500, 600, 700, 800, 900 µM, 1 mM and all the numbers in between.

In certain aspects, the leukocyte samples are pre-treated with permeabilization buffer first to allow the impermeant dyes to enter the leukocyte membranes. The incubation temperature ranges between 18° C. to 40° C. and the incubation time ranges between 5 minutes to 30 minutes, such as 1-10 minutes.

In still other embodiments, incubation times can range from about 30 seconds to about 20 minutes, but about 15 minutes is generally enough time for staining. Another desirable aspect of this invention is that optionally, in WBC analysis, any red cells in the biological sample may be lysed by standard techniques. Lysis of the red cells does not adversely affect this method. After the cell populations in the sample are adequately stained, the sample is excited with light at two wavelengths. According to the methods of this invention, fluorescence emitted from one white cell subpopulation is distinguishable from the fluorescence emitted from other white cell subpopulations in the same sample.

In certain embodiments, the use of the dye reagent comprises the following steps. About 5 µl human whole blood is first mixed with 5 µl permeablization buffer such as the Invitrogen Cal-Lyse™ solution for 5 minutes. Afterwards, the sample is mixed with 45 µl distilled water for 3 minutes and then buffered by 7 µl 10× concentrated Phosphate Buffered Saline. Finally, 10 µl of the dye mixture is added to the sample with a final concentration of 11 µM Propidium, 46 µM Basic Orange 21, and 14 µM Fluorescein Isothiocyanate and incubated with the sample for 15 minutes. In other aspects, the composition can dilute the sample or blood sample to a proportion of 10:1, 50:1, 100:1, or 1000:1 or any value in any of the above ranges, so long as the dilution meets the requirements of practical use. Such adjustment is within the capability of those skilled in the art with the aid of the present disclosure.

The blood samples stained by the dye reagent are flowed through a flow cytometer, where stained cells are exposed to excitation light source and the intensities of the two color fluorescence from leukocyte cells are recorded. In a scatter plot, leukocytes forms distinguished clusters relating to different leukocyte types including lymphocytes, monocytes, neutrophils, eosinophils and basophils. When blood samples are flowed through the detection channel, leukocyte cells are exposed to the excitation light one by one, and the two color fluorescence (red fluorescence and green fluorescence) from each individual leukocyte cell are recorded according to the fashion of the above method, where the total number of leukocyte cells are enumerated and different types of leukocytes are classified to achieve the leukocyte differential count.

Figure 4:
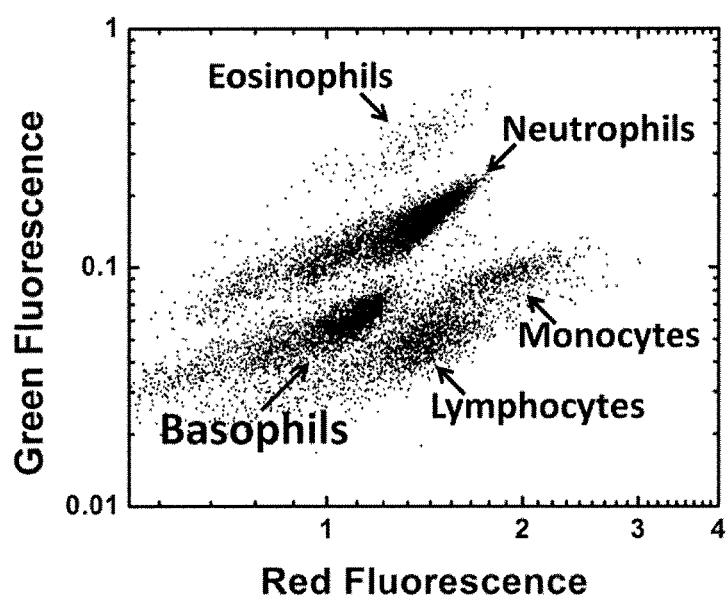
FIG. 4 shows a scatter plot of classifying different types of leukocytes with the two color fluorescence.

In certain embodiments, the measured intensities of all leukocyte cells are then displayed as a scatter plot, as shown in FIG. 4, where each point represents a counted leukocyte. The scatter plot shows four distinct clusters. The top cluster, which has the highest green intensity, consists mainly of eosinophil cells, while the middle cluster, which has medium green fluorescence, consists primarily of neutrophil cells, and the bottom two clusters are formed by lymphocytes cells and monocyte cells. The eosinophil cells are rich in acidophilic granules, which have high affinity binding to the third dye or the anionic dye, (e.g., FITC), and hence show the highest green fluorescence intensity. The neutrophil cells contain neutral granules, which have relatively lower affinity of FITC than eosinophil granules, but still provide a certain amount of protein content for FITC staining. The lymphocyte cells and monocyte cells have fewer granules and hence the lowest FITC staining intensity. Meanwhile, the monocyte cluster can be distinguished from the lymphocyte cluster by its higher red intensity and slightly higher green intensity. This is because the monocyte cells tend to have a larger amount of nucleic acid which is stained by the first dye (e.g., PI), and a larger amount of acidic cytoplasm content which is stained by the second dye (e.g., BO21).

In certain aspects, the fluorescence parameters can be utilized to recognize various subgroups of white blood cells and acquire information about possible abnormal lymphocytes and immature granulocytes, to classify and count the dots of various clusterings, and to calculate the percentages of various subgroups of white blood cells. For example, in one aspect, the fluorescence reflects the degree of granularity inside the cells. The degree of granularity of different subgroups of white blood cells is roughly as follows: the eosinophils have two foliate nuclei and many cytoplasmic granules that can be stained by acidic fluorescent dyes; the neutrophils have foliate or bacillar nuclei and more intracellular granules; the monocytes have a single big nucleus and less intracellular granules; and the lymphocytes have a single big nucleus and essentially no granules.

Analysis of the white blood cell subpopulations in a blood sample provides useful information for the clinical diagnosis of a multiplicity of diseases. For example, the onset of a disease may be associated with a change in the proportion and amount of different types of white blood cells in the blood, accompanied by the occurrence of abnormal white blood cells such as abnormal lymphocytes and immature granulocytes, etc. Therefore, differentiation and analysis of various types of normal and abnormal white blood cells provides information regarding the latency, onset and development stages of a disease.

In another aspect, the present invention provides a detection kit useful for differentiation and counting of leukocyte types or subpopulations in a sample such as blood, and at the same time useful for recognition of abnormal white blood cells (such as abnormal lymphocytes and immature granulocytes) in the sample. The detection kit includes a leukocyte (white blood cell) differentiation or diagnostic composition as disclosed herein and instructions for use. Lysis buffer is optionally included. The white blood cell diagnostic composition may further include a red blood cell lysing agent. In one embodiment, the fluorescent dye compounds in the diagnostic composition exist in the form of a stock solution and is preserved in a separate container. In another embodiment, the fluorescent dye compound is formulated with a lysing agent as a single-component solution. The detection kit may include a separate fluorescent dye stock that is suitably sealed in at least one container. The detection kit can also include other white blood cell differentiation reagents for the differentiation of white blood cells in the sample (e.g., blood) and instructions on how to identify the white blood cells. The detection kit can further include a control sample or a series of control samples (e.g., negative and positive controls) that can be detected and compared with test samples. Each individual component of the detection kit can be sealed in a single container, and these containers, together with the instructions, can all be packed in a single package. Such detection kits may be useful for the differentiation and/or counting of various white blood cells in the blood.

II. Examples

Example 1 Tabulates the Results of a Classifying Method

Table 1 shows the results of using the present method to classify different types of leukocytes, including lymphocyte, monocyte, neutrophil, eosinophil, and basophil. Differential count means the percentage of one specific type of leukocyte, such as lymphocyte (lypho), monocyte (mono), neutrophil (neutron), eosinophil (eosino), or basophil (baso), among the total number of leukocytes. "Reference" means the results from the commercial hematology analyzer (Beckman Coulter LH750). "Measured" means the results from the present method.

TABLE 1

| | | Leukocyte Type | | | | |
|---|---|---|---|---|---|---|
| | | Lympho | Mono | Neutro | Baso | Eosino |
| Differential Count (%) | Reference | 19 | 5 | 44 | 30 | 2 |
| | Measured | 18 | 6 | 46 | 28 | 2 |

Figure 3:
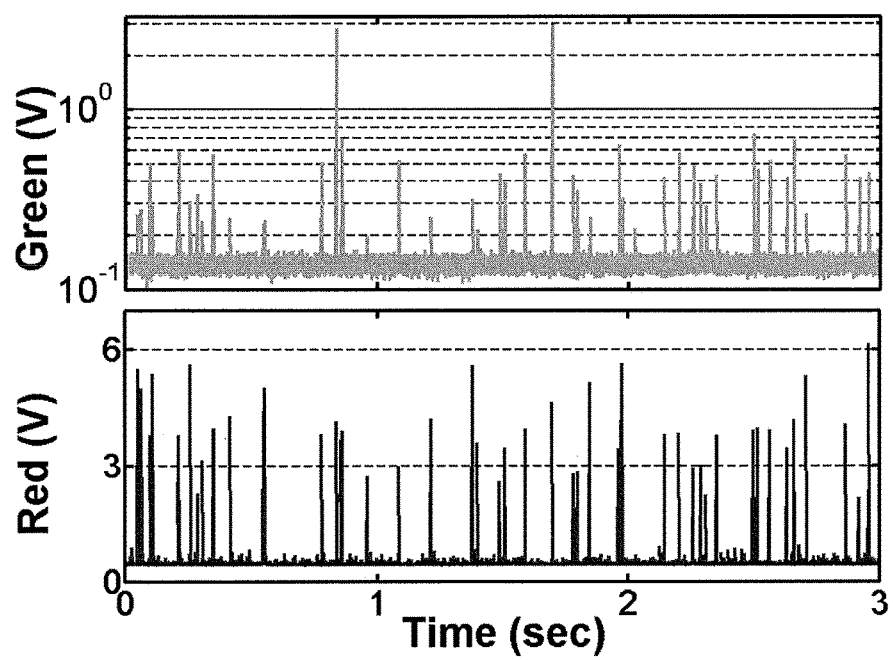
FIG. 3 shows the results of two color fluorescence signals measured from a sample stained with the present diagnostic composition.

FIG. 3 shows an example of the two color fluorescence signals measured from a sample stained with the present diagnostic compositor. The green fluorescence signal (the top trace) and the red fluorescence signal (the bottom trace) are measured simultaneously. Each distinguished peak in the red fluorescence signal represents one leukocyte being enumerated. The corresponding peak in the green fluorescence signal represents the fluorescence from the leukocyte's cytoplasm and protein contents stained by the dye reagent.

Example 2 Shows the Results as a 2-D Scatter Plot

The intensity of the red fluorescence and the intensity of the green fluorescence from individual leukocyte cell can be recorded as a two-dimension scatter plot (red fluorescence versus green fluorescence). FIG. 4 shows a scatter plot, wherein leukocytes types are shown as distinguished clusters relating to different leukocyte including lymphocytes, monocytes, neutrophils, eosinophils and basophils.

In the scatter plot, the eosinophil cluster appears sparse as compared with the other clusters. This can be attributed to the fact that eosinophil cells generally make up a much small percentage of all leukocyte cells in normal human blood (2% of total leukocytes in this example). Hence purified eosinophil cells can be used to validate whether the eosinophils are indeed localized in this cluster. In a control (whole blood) sample, the eosinophil cluster exhibits a relatively low density of cells. Meanwhile, after spiking the whole blood sample with eosinophil cells, the eosinophil cluster shows a higher density of cells, and the increase in the eosinophil count.

Figure 5:
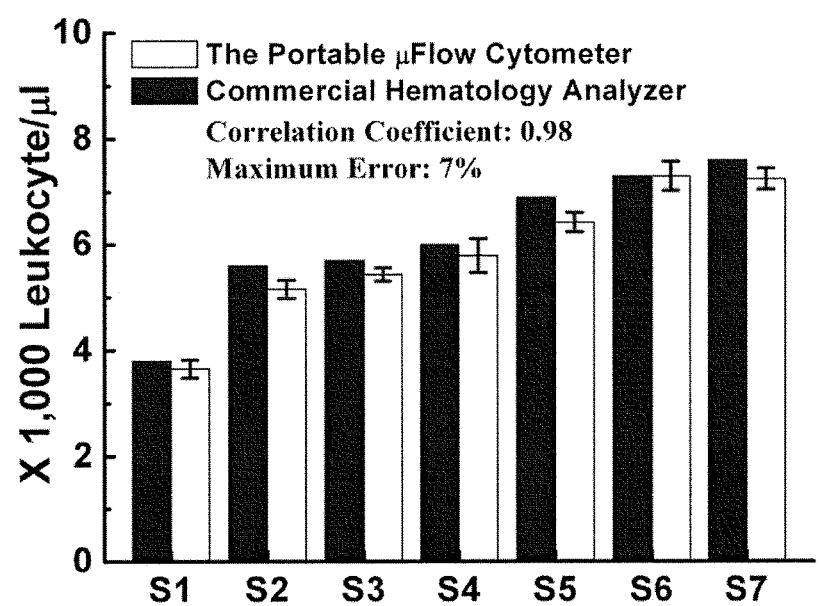
FIG. 5 shows a histogram enumerating total number of leukocyte in per volume blood using the present methods.

Example 3 Shows Comparative Results of the Inventive Methods and a Hematology Analyzer FIG. 5 shows an example of the results of enumerating total number of leukocyte. The results marked as "The portable μLow Cytometer" are results measured with the present method, and the results marked as "Commercial Hematology Analyzer" are results measured with a commercial Hematology Analyzer (Beckman Coulter LH750). S1, S2, S3, S4, S5, S6, S7 represents samples 1-7.

Figure 6:
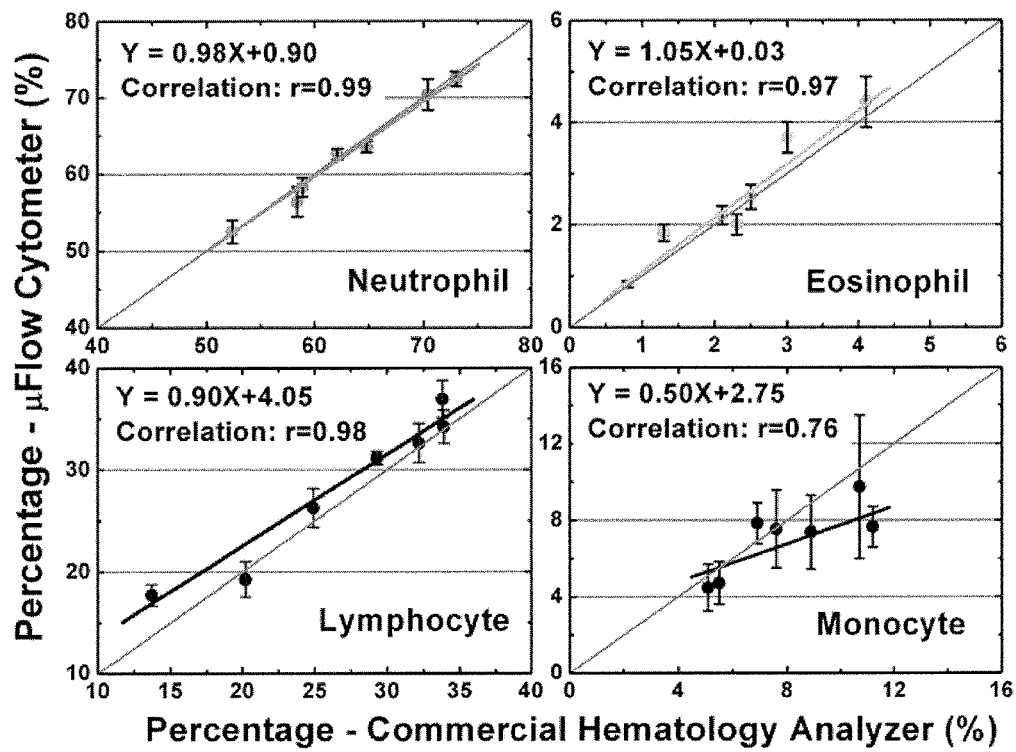
FIG. 6 shows a graph comparing the present methods against other available methods.

FIG. 6 shows an example of the differential result of classifying different types of leukocytes. The percentage means the percentage of one specific type of leukocyte, such as lymphocyte, monocyte, neutrophil or eosinophil, among the total number of leukocytes. The results marked as "μLow Cytometer" are results measured with the present method, and the results marked as "Commercial Hematology Analyzer" are results measured with a commercial Hematology Analyzer (Beckman Coulter LH750).

All publications and patents cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for classifying 5-leukocytes types in a leukocyte population with fluorescence detection, said method comprising:
   contacting a leukocyte population in a sample having one or more leukocyte types with a diagnostic composition, said diagnostic composition comprising:
   a first dye having a cationic charge, wherein said first dye is propidium iodide;
   a second dye having less cationic charge compared to said first dye, wherein said second dye is Basic Orange 21; and
   a third dye being reactive to a protein, wherein said third dye is fluorescein isothiocyanate having an affinity to a protein;
   exciting the stained leukocyte population with a light source; and
   measuring emitted light from each of the one or more leukocyte types to classify the leukocyte population, wherein the leukocytes in the population comprise a lymphocyte, a monocyte, a neutrophil, an eosinophil and a basophil.

2. The method for classifying of claim 1, wherein the fluorescence emitted from each of the leukocyte types is distinguishable from each of the other types in the population.

3. The method for classifying of claim 1, wherein the first dye primarily stains the nucleus of the one or more leukocyte types.

4. The method for classifying of claim 1, wherein the second dye primarily stains the cytoplasm of the one or more leukocyte types.

5. The method for classifying of claim 1, wherein the third dye primarily stains the protein content of the one or more leukocyte types.

6. The method for classifying of claim 1, wherein the excitation light is emitted from a source selected from the group consisting of a diode laser, a light emitting diode (LED), an ion laser, a dye laser, and a lamp.

7. The method for classifying of claim 6, wherein the emitted light is measured at a first wavelength and at a second wavelength to achieve two color fluorescence measurements.

8. The method for classifying of claim 7, wherein the emitted light is measured at the first and the second wavelength.

9. The method for classifying of claim 8, wherein the emitted light is measured simultaneously by two photomultiplier tubes.

10. The method for classifying of claim 1, wherein the sample is selected from the group consisting of whole blood, plasma, and serum.

11. The method for classifying of claim 10, wherein the sample is stained by the diagnostic composition and is flowed through a flow cytometer.

12. The method for classifying of claim 11, wherein the one or more leukocyte types are exposed to the light source, and the intensities of the fluorescence is recorded.

13. The method for classifying of claim 10, wherein the sample is stained by the diagnostic composition and is flowed through a microfluidic cytometer.

14. The method for classifying of claim 13, wherein the sample is flowed through a detection channel.

15. The method for classifying of claim 13, wherein the one or more leukocyte types are exposed to the light source one by one, and two color fluorescence emission from each individual leukocyte type is recorded.

* * * * *